(12) United States Patent
Fridental

(10) Patent No.: US 9,971,153 B2
(45) Date of Patent: May 15, 2018

(54) METHOD AND APPARATUS FOR DISPLAYING VIDEO DATA

(71) Applicant: Ron Fridental, Shoham (IL)

(72) Inventor: Ron Fridental, Shoham (IL)

(73) Assignee: FRIMORY TECHNOLOGIES LTD., Shoham (IL)

(*) Notice: Subject to any disclaimer, the term of this patent is extended or adjusted under 35 U.S.C. 154(b) by 866 days.

(21) Appl. No.: 14/229,874

(22) Filed: Mar. 29, 2014

(65) Prior Publication Data

US 2015/0277121 A1   Oct. 1, 2015

(51) Int. Cl.
| | |
|---|---|
| H04N 13/04 | (2006.01) |
| G02B 27/01 | (2006.01) |
| H04N 9/31 | (2006.01) |
| A61B 3/12 | (2006.01) |

(52) U.S. Cl.
CPC ............ G02B 27/0172 (2013.01); A61B 3/12 (2013.01); G02B 27/0101 (2013.01); H04N 9/31 (2013.01); H04N 13/042 (2013.01); H04N 13/044 (2013.01); H04N 13/0459 (2013.01); G02B 2027/014 (2013.01); G02B 2027/0134 (2013.01); G02B 2027/0138 (2013.01)

(58) Field of Classification Search
CPC ..... G06T 3/00; G06T 19/017; G02B 27/0093; H03M 13/356; H04N 13/026

USPC ................ 348/8, 43, 51, 345; 345/419, 420
See application file for complete search history.

(56) References Cited

U.S. PATENT DOCUMENTS

| | | | |
|---|---|---|---|
| 2004/0080661 A1* | 4/2004 | Afsenius | G02B 7/36 348/345 |
| 2005/0146521 A1* | 7/2005 | Kaye | G06T 3/00 345/419 |
| 2006/0232665 A1* | 10/2006 | Schowengerdt | G02B 27/0093 348/51 |
| 2010/0020160 A1* | 1/2010 | Ashbey | H04N 13/026 348/43 |
| 2013/0194259 A1* | 8/2013 | Bennett | G06T 19/006 345/420 |
| 2014/0184475 A1* | 7/2014 | Tantos | H03M 13/356 345/8 |
| 2014/0267941 A1* | 9/2014 | Ellsworth | G02B 27/017 349/5 |

* cited by examiner

*Primary Examiner* — Gims Philippe
(74) *Attorney, Agent, or Firm* — Soroker Agmon Nordman

(57) ABSTRACT

A method and devices for displaying images, the method comprising: receiving an image, the image comprising depth information; determining at least a first group of pixels and a second group of pixels, based on the depth information; and displaying the first group of pixels at a first focus position of the projection device, and the second group of pixels at a second focus position of the projection device.

9 Claims, 8 Drawing Sheets

METHOD AND APPARATUS FOR DISPLAYING VIDEO DATA

CROSS REFERENCE TO RELATED APPLICATIONS

None

STATEMENT REGARDING FEDERALLY SPONSORED RESEARCH OR DEVELOPMENT

Not Applicable.

REFERENCE TO SEQUENCE LISTING

Not Applicable.

TECHNICAL FIELD

The present disclosure relates to video cameras and projectors in general, and to a method and apparatus for high quality display of video data, in particular.

BACKGROUND

A video projector is an image projector that receives a video input signal and projects the corresponding image. Video projectors are widely used for many applications such as but not limited to conference room presentations, classroom training, home theatre and concerts. Emerging video projection applications are applications related to wearable head mounted displays used for displaying videos, games, which may also be used as a generic computer and smartphone display interface with both conventional and novel display features, such as eye tracking and other. Video projectors may be connected to and receive video signals from a wide variety of sources.

The video projector receives a video signal and projects the corresponding image or sequence of images onto a projection screen, a retina of the user's eye in the case of head mounted displays, or another object or area (collectively referred to as projection screen). The video projector comprises an image-forming element, also referred as an active matrix, which forms an image that corresponds to the video signal, and an optical system that projects the image and focuses it onto the screen, eye retina or other object.

An important issue related to image quality in the field of video projectors is the need to simultaneously focus the entire projected image. This problem is caused by the differences of the distance between the video projector and various areas of the projection screen. In 3D applications related to head mounted displays, such as displaying the 3D video stream, augmented reality, stereo films or others, a related but even harder problem may exist, when it is desirable to focus different parts of the image at different focal lengths.

Known solutions to the problem include using a flat screen having under the right conditions almost uniform distance from the video projector. However, this solution limits the type of applications that can be implemented.

Alternative solutions relate to partially closing the lens aperture in order to increase the depth of focus. However, closing the aperture decreases the projector brightness, and thus reduces the viewing quality or the power efficiency.

The problem of focusing different parts of image at different focal lengths is significant in the field of head mounted displays (HMDs) and optical head mounted displays (OHMDs). HMDs are wearable video displays shaped as a helmet, a pair of glasses or in any other shape, projecting a separate video stream into each eye of the user. OHMDs are wearable displays with a semitransparent optical element reflecting the projected images into the user's eyes as well as allowing the user to view the surrounding physical environment through it.

One application of HMD is displaying 3D content to a user. Humans perceive the 3D via two major clues: the stereo disparity between the images perceived by the right and the left eyes, and the difference in the optical distance matched by the appropriate optical accommodation of the eyes. Conventional 3D displays provide only one clue—the stereo disparity, where the 3D effect is achieved by projecting different content to the left and to the right eyes. For example, prior art 3D TV sets, 3D movies in cinemas, and 3D HMD project at the same fixed distance, which may be the distance to the TV screen, to the screen in the movie theatre, or o the image focal plane in the HMD. The lack of means to present a second 3D clue, namely the varying focus distance matching the 3D stereo disparity, decreases the 3D effect of the projected content. Furthermore, it severely undermines the performance of HMD in some applications.

Another application of HMD and OHMD relates to augmented reality, wherein the displayed content is associated with the real world perceived through the optical element or captured by a camera, recreated by the device and augmented with additional video content. In the case of OHMD the user perceives the world with objects being at different distances, wherein the augmented layer imposed over the perceived world in the prior art OHMD has only one focal distance. This focal distance may coincide with some objects of the real world, but may mismatch closer or farther objects.

The focusing of the human eye to the particular distance of the perceived object may be referred to as accommodation. Due to limited depth of focus of the eye, and the accommodation of the human eye, the user will focus either on object, and see the imposed layer as blurred, or on the layer, and see the objects blurred

BRIEF SUMMARY

One exemplary embodiment of the disclosed subject matter is a method for displaying images by a projection device, comprising: receiving an image, the image comprising depth information; determining at least a first group of pixels and a second group of pixels, based on the depth information; and displaying the first group of pixels at a first focus position of the projection device, and the second group of pixels at a second focus position of the projection device. Within the method, the projection device is optionally a head mounted display. Within the method, the projection device is optionally an optical head mounted display, allowing to simultaneously perceive the projected video and an environment of the projection device. Within the method, the depth information is optionally computed from the environment underlying the projected image. The method may further comprise repeating said receiving, said determining and said displaying for a multiplicity of images of a video stream, wherein the video stream is displayed at a frame rate of about at least 10 frames per second. Within the method, the video is optionally a stereo video, comprising a left eye channel and a right eye channel, and having stereo disparity between the left eye channel and the right eye channel, wherein a first sequence comprising images to be displayed to a left eye of a viewer and a second sequence rising images to be displayed to a right eye of the viewer, are optionally retrieved from the video, wherein the depth information is optionally determined from stereo disparity between the images to be displayed to the left eye, and the images to be displayed to the right eye, and wherein said displaying optionally comprises projecting the first sequence to the left eye of the viewer, projecting the second sequence is projected to the right eye of the viewer.

Another exemplary embodiment of the disclosed subject matter is a projecting system, comprising: an active matrix for forming an image to be projected; and an optical system for projecting the image onto a screen, wherein a focal distance of the optical system is adapted to change during display time of the image. Within the projecting system, pixels in a first group of pixels in the image are optionally turned on when the optical system assumes a first focus position, and are off at other focus positions, and pixels in a second group of pixels in the image are optionally turned on when the optical system assumes a second focus position and are off at other focus positions. Within the projecting system, a first group of pixels in the image is optionally displayed when the optical system assumes a first focus position and a second group of pixels in the image is optionally displayed when the optical system assumes a second focus position.

Yet another exemplary embodiment of the disclosed subject matter is a video projection system, comprising: an active matrix for forming an image to be projected; an optical system for projecting the image onto a screen; and a feedback image sensor, and a semitransparent mirror, placed so that the active matrix and the feedback image sensor forming equivalent optical paths relatively to the semitransparent mirror. Within the video projection system, an image reflected from the screen and acquired by the feedback image sensor is optionally used to control operation parameters of the video projecting system. Within the video projection system, the image is optionally projected onto an eye retina of a viewer, and information acquired by a feedback image sensor is optionally used to control operation parameters of the video projecting system for image focusing or for alignment on the retina. The video projection system is optionally comprised in a device wearable by a viewer.

Yet another exemplary embodiment of the disclosed subject matter is a vision aid apparatus, comprising: at least one video camera for acquiring a video stream of an environment of the apparatus; a processing unit for processing the captured video; and a head mounted display, comprising an image forming active matrix and projecting the acquired video stream onto a retina of an eye of a user, wherein the vision aid is wearable by the user. Within the vision aid apparatus, the at least one video camera optionally comprises a first video camera and a second video camera, video captured by the first video camera is optionally projected into a left eye of the user, and video captured by the second video camera is optionally projected into a right eye of the user. Within the vision aid apparatus, the processing unit processes the video to change one or more projection parameters, each projection parameters selected from the group consisting of: color spectrum, brightness, and layout geometry. The vision aid apparatus optionally comprises a feedback image sensor and a semitransparent mirror placed diagonally between the image sensor and the active matrix, to form optically equivalent paths between the image sensor and the active matrix relatively to the said mirror. Within the vision aid apparatus, the processing unit optionally distorts images of the video stream to remap the images onto at least one sensitive part of the retina, and wherein the feedback image sensor is adapted to control alignment of the image on the retina during eye motion.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
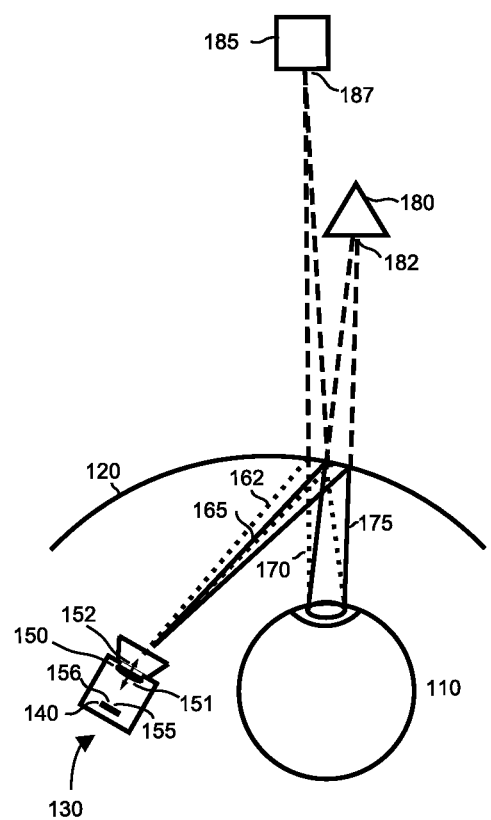
FIG. 1 is a schematic illustration of a 3D video projector, in accordance with some embodiments of the disclosure.

The disclosed subject matter is described below with reference to flowchart illustrations and/or block diagrams of methods, apparatus (systems) and computer program products according to embodiments of the subject matter. It will be understood that each block of the flowchart illustrations and/or block diagrams, and combinations of blocks in the flowchart illustrations and/or block diagrams, can be implemented by computer program instructions and/or electronic circuit. These computer program instructions may be provided to a processor of a general purpose processor, application processor, application specific integrated circuit, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

One technical problem dealt with by the disclosed subject matter is that an image projected by a video projector may contain areas having different focal distances, or that should be projected such that they are perceived at particular distance from a viewer, while current projectors project the whole image with a single focal distance. Optical systems of prior art HMDs have a focusing element, allowing to adjust the perceived focus of the displayed image to a focal length convenient for the user eye. However, the focusing element makes the entire displayed image focused at the one particular focal distance. This is sub-optimal in regular video, but even more so when displaying 3D content, and is particularly annoying in augmented reality applications of OHMD. While the surrounding real-world objects perceived through an optical element of OHMD naturally have different distances, the additional video layer displayed by the existing OHMD has a single focal distance, thus creating an uncomfortable and unrealistic feeling.

The human eye accommodates its focal distance to focus on the objects situated at different distances. Therefore, a human user can not perceive objects located at significantly different distances as being sharp simultaneously. Thus, in augmented reality applications, if an image to be projected overlaying a real world object is perceived at a different distance than the underlying real world object, a viewer may perceive either the projection or the object as blurred.

Therefore for enhanced perception results the projector should project an overlying image at the same optical distance as an underlying object, to prevent either the object or the imposed image from being perceived as blurred.

One technical solution of the disclosed subject matter relates to displaying different parts of an image such as a video image (also referred to as a frame) at different focal distances, such that each area of the image is displayed at the focal distance that corresponds to the content of the area. In some embodiments, a video projector is equipped with a moving focusing element or with a focusing element capable of changing its focal length, which when moved throughout its possible focus positions or focal values may provide substantially the entire focal range required for the projection at all possible focal distances. For example, the projector may be required to change the effective focal value from about perceived 10 cm to perceived infinity, during the display period of a single frame. However, it is understood that in some embodiments or applications the required focal range may be greater, for example in order to make an optical correction for user Nearsightedness (Myopia) or Farsightedness (Hyperopia).

The focusing element may be an optical lens which can be moved along the optical axis of the lens. Additionally or alternatively, the focusing element may be a lens or a mirror the shape of which can be changed, or any other element or mechanism that can change the effective focal length of the optical system. In disclosure below the terms focus change, focal position change and similar terms refer to changing the effective focus of an optical element, and the terms focal length, focal distance or focal position may be used interchangeably.

In accordance with some embodiments, a projecting optical system may change its focal length periodically, at the frequency equal or related to the frame rate of projected video. An image forming element of the projector may display different groups of image pixels during different sub-periods of the image frame display time, so that only those areas of the image having a focal length corresponding to the focal length provided by the moving focusing element at that sub-period are displayed. Thus, an area of the frame is displayed only when the projector is in substantially a corresponding focal length for the area. This results in different parts of a single projected image, or a single frame, being displayed at different focal positions and at different times, such that areas of the image may be displayed for only a part of the frame period, when the focusing element is at appropriate focus position. However, at sufficiently high frame rate for example about 10 frames per second or more, due to the averaging property of the human visual perception, the entire image is perceived as though it is displayed continuously, with each sub-part of the image being displayed continuously and at the appropriate focal length.

It will be appreciated that the focus change may be performed by a harmonic function law, piecewise linear, in steps, or in accordance with any periodic or repeating function.

An image in accordance with the disclosure may comprise depth information. The depth information may be provided as an additional layer of a 3D image. Alternatively, the depth information may be determined from data within the image which may be acquired by applying image processing techniques, from data within a video flow comprising the image, from data acquired by a 3D scanner, or from any other source. For example, in a stereo flow with two channels having stereo disparity therebetween, depth information may be determined from the stereo disparity, as known in the art.

Another technical solution relates to a three-dimensional (3D) HMD, which according to some embodiments of the disclosure may operate as follows. The device may be equipped with a focusing element such as a lens which may assume a multiplicity of focal distances. The focus range of the lens, i.e., the focal distances provided by the device may be divided into several sub-ranges. Each 3D frame to be displayed may be divided into several sub-frames, so that each sub-frame comprises pixels to be projected with the corresponding depth sub-range. The focusing lens sweeps over the range during the display time of each video frame, and the corresponding sub-frames may be displayed at corresponding focal distances of the focusing lens. It will be appreciated each sub-frame may comprise zero or more pixels at various coordinates of the frame.

Each pixel of the displayed image may be active, e.g., switched on during the parts of the display time at which the focus is appropriate for that pixel, i.e., the lens position is at a focus appropriate for the given pixel, and passive, i.e., switched off during the rest of the display time, which may account to most of the display time. Alternatively, active pixels may be displayed with a first brightness level and inactive pixels may be displayed with a second brightness level, lower than the first brightness level. In some embodiments the first brightness level may be substantially equal to a nominal brightness level of the pixel, and the second brightness level may be equal to a minimal brightness level, such as zero brightness level.

Due to the time averaging of the human perception, at sufficiently high frame rate, such as about 10 frames per second or higher, a user perceives all pixels as constantly active, wherein each pixel or pixel group has a particular focal distance in space.

Yet another technical solution relates to a method for controlling the quality of an image projected onto the retina of a user's eye, as done for example by a wearable devices such as HMD glasses. An image is projected onto the retina, and reflected back through an optical system which may share components with the projection optical system. The reflected image may be redirected by a semitransparent mirror to a feedback image sensor. The semitransparent mirror may be placed diagonally between the active matrix and the image sensor, so that the active matrix and the image sensor have equivalent optical paths relatively to the semitransparent mirror and the optical system. Therefore the sharp image projected on the screen or the retina will form the sharp image on the image sensor, allowing to monitor the projection quality. Video acquired by the said feedback image sensor may then be processed, allowing to monitor the image projected on the user's retina, its sharpness, location relative to the retina or other parameters. The location of the projected image relative to the retina may be controlled via the image processing, taking into account the image details and the retina natural patterns such as blood vessels or other ques. The focus position of a lens of the projector at which the image is sharpest may be determined, and the projection may be adapted accordingly by either projection of the pixels during the subintervals of the frames when the focusing lens assumes appropriate focus values, or by fixing the focusing lens at these appropriate focus values.

One technical effect of the disclosure relates to projecting image parts for a fraction of a frame display time, and at focal distances such that the entire projection can be focused even on objects requiring different focal length for different parts of the image.

Another technical effect relates to projecting image layer over the environment perceived through a semitransparent element of an OHMD. The different regions of the image projected at different focal distances such that each image part has the same focal distance as an underlying object in the environment. Such solution may provide for augmented reality applications in which image parts are projected to visually coincide in distance with underlying real world objects. Such solution may also provide for projecting 3D video.

Yet another technical effect may relate to enhancing sharpness of pixels in a frame projected onto a user's retina by displaying each pixel or pixel group at a position of the lens in which their focusing on the retina is sharpest. This allows for coping with the problem of human eye accommodation, in which when due to refocusing of the eye, the images displayed by the video projector continuously slip out of focus.

Yet another technical effect may relate to enhancing images in accordance with an ophthalmologic characterization of a user's eye. Such solution may be used for implementing a vision aid in which the user sees the environment via the device, wherein the device acquires the view of the surrounding environment, via one or more cameras, wherein the view is processed in accordance with the user's eye characteristics.

In particular, in some embodiments the disclosure may be used in the following mode: One or more environment cameras may capture the environment, the captured video is possibly processed in accordance with problems and limitations of the user vision, and then immediately re-projected onto the user's eyes. The corrections may include any one or more of the following: change of the color spectrum to enhance the color sensitivity or to display invisible optical bands such as infrared or ultraviolet; distort the image to project it onto active sensitive parts of the retina, to improve the field of view for persons with limited field of view; adding projection from side- or rear-facing cameras; amplification of the signal to improve the night vision capabilities; addition of high dynamic range imaging, or other multiple enhancements implemented in hardware, software or a combination thereof.

Referring now to FIG. 1, showing an embodiment of a 3D video projector in accordance with some embodiments of the disclosure. The video projector, generally referenced 130 comprises an image forming matrix 140 and one or more optical components such as a focusing lens 150 which is capable of being moved along range 151 between a starting point and an end point. Alternatively, the system focus may be changed by another means. A mirror, semitransparent mirror or another image projecting element 120 may be positioned in front of the viewer's eye.

When pixel 155 generated by image forming active matrix 140 is projected, beam 162 is created by lens 150.

When beam 162 hits mirror 120, it is reflected as beam 170 into the user's eye. The user perceives point 187 which is continuation of beam 170 as the point in space corresponding to pixel 155. It will be appreciated that beams 162 and 170 are each indicated by two rays for visualization purposes and in order to demonstrate the focusing on point 187.

As the focus of lens 150 changes, the perceived distance of a sharp projected point changes correspondingly. Pixel 187 in space corresponds to pixel 155 and its vicinity, and focus position 151 of lens 150. Pixel 182 in space corresponds to lens focal position 152, and to pixel 156 on the active matrix.

In one embodiment of present invention, lens 150 periodically moves between extreme focal positions, and its movement range includes positions 151 and 152. Pixel 156, corresponding to point 182 on object 180 in space is switched on when the lens is in position 152, and switched off during other positions of the lens, while pixel 155, corresponding to point 187 on object 185 in space is switched on when the lens is in position 151, and switched off during other positions of the lens.

Thus, in augmented reality applications, in which an image is perceived as projected onto the environment, the images imposed onto the real world objects are perceived at the same focal distance as the underlying objects.

Figure 2:
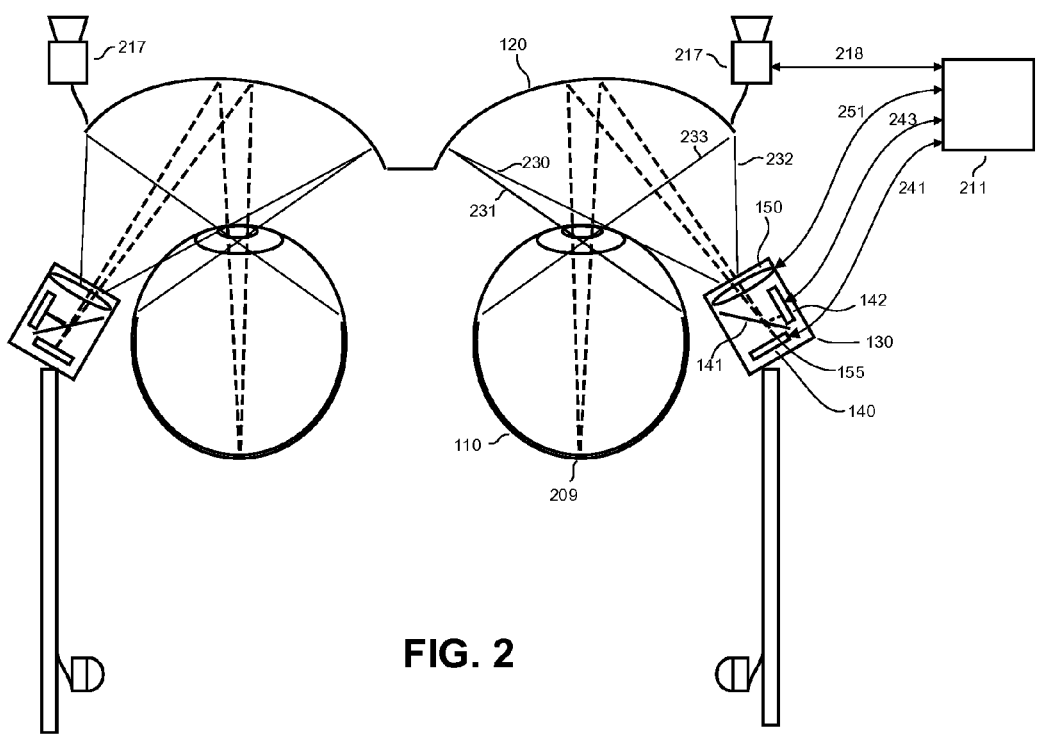
FIG. 2 is a schematic drawing of a head mounted display and optical head mounted display, in accordance with some embodiments of the disclosure.

Referring now to FIG. 2, showing a schematic drawing of a head mounted display and its optical mode of operation, in accordance with some embodiments of the disclosure. The HMD is adapted to project images onto the retina of a user. The HMD may comprise semitransparent mirror 120 used to overlay an image projected by the HMD on the direct view of the surrounding physical environment. In other embodiments other types of projecting element 120 may be used.

One or more video cameras 217, a 3D scanner or any other video source may be used to provide frames to processing unit 211 for analyzing the frames, retrieving depth information, processing for further re-projection onto the eyes, or adding an augmented reality layer to the environment as directly perceived by the user, or the like. Video projecting unit 130 may comprise an image forming active matrix 140 for projecting the frames provided by processing unit 211 as well as an image to be overlaid on the frames. Video projecting unit 130 may further comprise focusing element 150. When a pixel from image active matrix 140 is projected, a beam is created and may pass through an optional semitransparent mirror 141, and is reflected onto pixel 209 on the user's retina from a mirror or semitransparent mirror 120. Semitransparent mirror 120 is used to overlay an image projected by the HMD on the direct view of the surrounding physical environment in augmented reality applications. In another embodiment the transparency of element 120 may vary, up to completely non-transparent mirror. It will be appreciated that other configurations may be used which do not include mirror 120, and which may comprise another type of projecting element instead of it. If mirror 120 is permanently non-transparent, or a semitransparent mirror of varying transparency in a non-transparent state, the HMD may project a desired video content, including a real-time video of the environment captured by cameras 217. The beam returned from the user's eye retina is reflected back by semitransparent element 120, passes backward through optical focusing element 150 and reflected by diagonal semitransparent mirror 141 onto a feedback image sensor 142. Feedback image sensor 142 may record the image as received from the retina and pass it for processing, in order to control the image focusing, location or alignment on the eye retina, diagnose the condition of the retina or the eye, or for any other purpose.

The HMD in accordance with FIG. 2 thus projects images onto the user's retina, and also receives back the images as projected in order to assess or control their sharpness, alignment, brightness or other parameters.

It will be appreciated that projecting unit 130 may also comprise a controller for focusing lens 150 along a range such that it assumes at least two different positions, and for activating the pixels relevant for each lens position and deactivating the other pixels. The controller may be implemented as part of image processing unit 211.

It will be appreciated that a corresponding structure may also be provided for the other eye of the user. It will be further appreciated that the frames provided to the image processing or controller unit 211 may comprise image pairs designed to create a 3D effect, by stereo disparity between the right and the left images, and that operation of video projecting unit 130 may further enhance the stereo effect by projecting each pixel at the focus corresponding to its stereo disparity.

Figure 3:
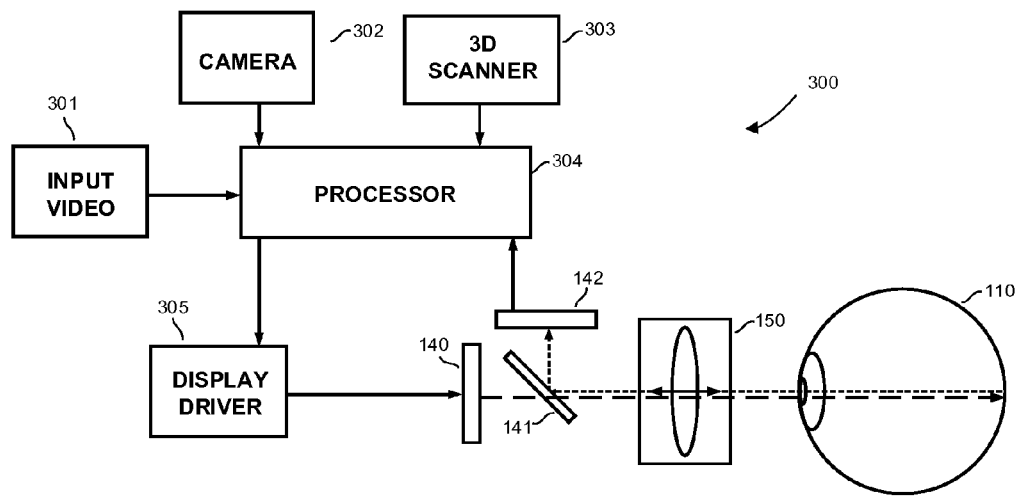
FIG. 3 is a schematic illustration of a 3D projector with image feedback sensor, in accordance with some embodiments of the disclosure.

Referring now to FIG. 3, showing a schematic block diagram of a video projection device, in accordance with some embodiments of the disclosure. The projection device may be an implementation of device 130 of FIG. 2. The projection device, generally referenced 300 comprises a processor 304, for receiving or controlling the inputs from input video inputs 301, one or more video cameras 302, a 3D scanning system 303 or any other video source.

Processor 304 may be an Application Processor, a Central Processing Unit (CPU), Application Specific Integrated Circuit (ASIC), a microprocessor, an Integrated Circuit (IC) or the like. Alternatively, computing processor 304 can be implemented as firmware written for or ported to a specific processor such as digital signal processor (DSP) or microcontrollers, or can be implemented as hardware or configurable hardware such as field programmable gate array (FPGA).

After possible processing of the video input, processor 304 may form a multiplicity of frames. Processor 304 may then transmit the video frames to display driver 305, which forms a time sequence of image frames on active matrix 140. Each frame is to be transmitted through semitransparent mirror 141 and focusing element 150, and directed onto the retina of a user's eye 110. Optional semitransparent mirror 141 redirects the image reflected back from the retina into feedback image sensor 142. The optical paths from active matrix 140 and from feedback image sensor 142 towards semitransparent mirror 141 are equivalent, so that if the image displayed on active matrix 140 is projected sharp onto the retina, it will also form a sharp secondary image on feedback image sensor 142. Therefore the feedback image may by further processed by processing unit 304, and may be used to control the sharpness, alignment on the retina and other properties of the projected image in one or more ways, including but not limited to the following:

(A) Improving the projection sharpness. The accommodation of the human eye changes the eye's focal length. Therefore in order to maintain sharp projection, the focus of the projector should change accordingly. The correct focal position can be found by the following procedure. The image is projected onto the retina while focusing element 150 performs a sweep throughout the entire focal range, and the feedback sensor acquires a sequence of the feedback images along the way. The sharpness of each of the feedback images is evaluated, and the sharpest image is determined, as well as the corresponding position of the focusing element 150. One or more frames are then projected with focusing element 150 at this position. Common nominal projection frame rate may be about 10 frames per second, or higher. This frame rate provides for a period of projection of a single frame varying from about 100 milliseconds for the slowest frame rates, to less than 1 ms for high frame rates. The user's eye may change the accommodation, after which a different focal length will be required for sharp projection. Since the accommodation process of the eye is slow, typically taking hundreds of milliseconds, each focusing of the projection lens can suffice for sharp projection of multiple frames. Furthermore, the sweep of the lens and search for optimal focal position can be performed at accelerated frame-rate, and/or reduced projected brightness followed by reduced frame rate or increased brightness for the longer part of the frame display time.

(B) Remapping or geometrically distorting of the environment view in order to compensate for blind areas on the retina. Some people suffer from a limited field of view, due to some parts of their retina being non-sensitive, for example as a consequence of a stroke or other illness. The apparatus of FIG. 3 may be utilized in a system such as the HMD on FIG. 2 which may be used as a vision aid. In such application, element 120 may be non-transparent, and the video projector may recreate the environment as captured by cameras 217. For a user with limited field of view, the environment image may be scaled, geometrically distorted or remapped such that the entire image is projected only onto the functional parts of the retina. While prior art HMDs cannot project an image and keep the image projected onto only specific parts of the retina due to the eye motion relatively to the video projector, in a projector in accordance with the present disclosure, the use of feedback image sensor 142 allows capturing the image as projected onto the retina. Processing the feedback image allows for detecting patterns of the retina blood vessels or other visual ques. The position of the projected image relatively to the eye retina may be determined from these queues, which may enable adjusting the projected image and remapping it in the appropriate way.

(C) Remapping the color map or other features. Other applications of a vision aid device in accordance with the disclosure may operate by acquiring the environment by cameras 217 and re-projecting the environment video onto the eye retinas, using configurations in which element 120 is non-transparent. In some embodiments, the video may be processed as follows: the color spectrum may be remapped wherein the spectrum of the colors for which the user vision is non-sensitive may be shifted into areas of the spectrum to which the user vision is more sensitive; users with darkness blindness who are unable to see in low illumination, may be provided with image brightness amplification; high dynamic range imaging (HDR) can allow simultaneous vision of very bright and very dark object; may be used when displaying invisible spectrums such as infra-red or ultra-violet; normally un-perceived directions may be projected as well, for example by using rear facing cameras, which video is added into the primary video; resolution may be improved for example, by a binocular, or on the contrary—ultra wide view may be provided; auxiliary layers may be added to display sensor data such as distance, information about the people based on their recognition, identification and social network profiles; automatic translation of text in foreign languages; adding additional information about products in a store, animals, plants, or other objects, navigation aid, and other existing and to be developed software.

Images captured by the feedback sensor 142 may be further used. For example, by continuously sweeping focusing lens 150 and searching for the position where the image on the retina is best focused allows for maintaining a sharp projected image despite change of focus (accommodation) of the user's eye. During the focusing movement of lens 150, the acquisition frame rate of the feedback sensor 142 may be accelerated, or the brightness of the image projected by the active matrix 140 may be decreased.

It will be appreciated, that focusing element 150 may change the focal distance of the system by any other mechanism, and is not limited to lens movement.

It will be appreciated that active matrix 140 and feedback sensor 142 may be placed at the same distance from semi-transparent mirror 141, so that they form equivalent optical paths with focusing element 150 up to reflection from or passing through semitransparent mirror 141. That allows for using the image formed on feedback sensor 142 for adjusting the focus and layout of the projection on the screen or retina, of images displayed by active matrix 140.

It will be appreciated, that although FIGS. 1, 2, and 3 show video projectors related to head mounted displays, the present disclosure is not limited to projection onto the retina of the eye, and is applicable to any still image or video projecting device, including movie projectors, home theatre systems, projection on any screen, or others.

Figure 4:
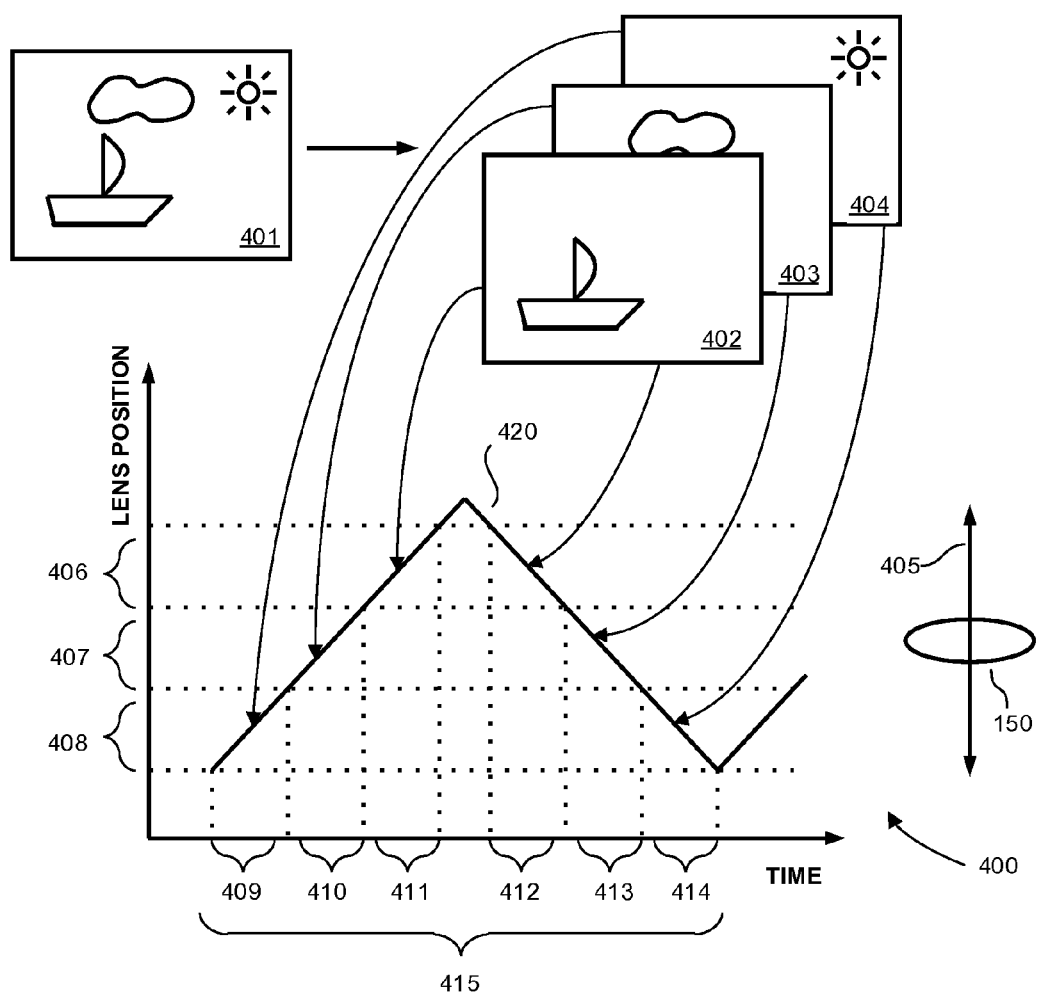
FIG. 4 is an illustration of the projection of different parts of an image at different focal lengths, in accordance with some embodiments of the disclosure.

Referring now to FIG. 4, showing a schematic illustration of the operation principle of some embodiments of the disclosure. Input frame 401 comprises a number of areas, wherein each area depicts objects in a different focus range. Frame 401 may be analyzed, and its pixels may be divided into groups according to the required focus distance. For example, the boat is at a first focus distance, the cloud is at a second one, and the sun is at a third. The required focus distance may be derived either from depth information supplied with the frame, from stereo disparity for the stereo frames consisting of right-eye and left-eye pairs, from 3D analysis of the frame and objects thereon, from the distance of surrounding physical objects for frames which are overlaid onto the direct view of the physical environment in augmented reality scenario, or in any other manner.

Subframe 402 contains the pixels of frame 401 which are in close range, subframe 403 contains the pixels of the mid-range, and subframe 404 contains the pixels of the remote range. The number of subframes may vary, depending on the implementation, application, particular image or other factors.

The plot in the lower part of FIG. 4, generally referenced 400, denotes the change of focus distance vs. time. The vertical axis indicates the focal distance which corresponds to the position of the lens, as schematically shown by lens 150 moving along range 405. The horizontal axis corresponds to time. Graph 420 represents the lens position motion. Time interval 415 represents a period of one frame, divided into sub-periods 409 . . . 414. Time periods 409 and 414 correspond to remote focusing range 408, during which subframe 404 having the remote focus distance is displayed; periods 410 and 413 correspond to middle focusing range 407, during which the subframe 403 having the middle focus distance is displayed; and periods 411 and 412 correspond to near focusing range 406, during which subframe 402 having the near focus distance is displayed.

Figure 5:
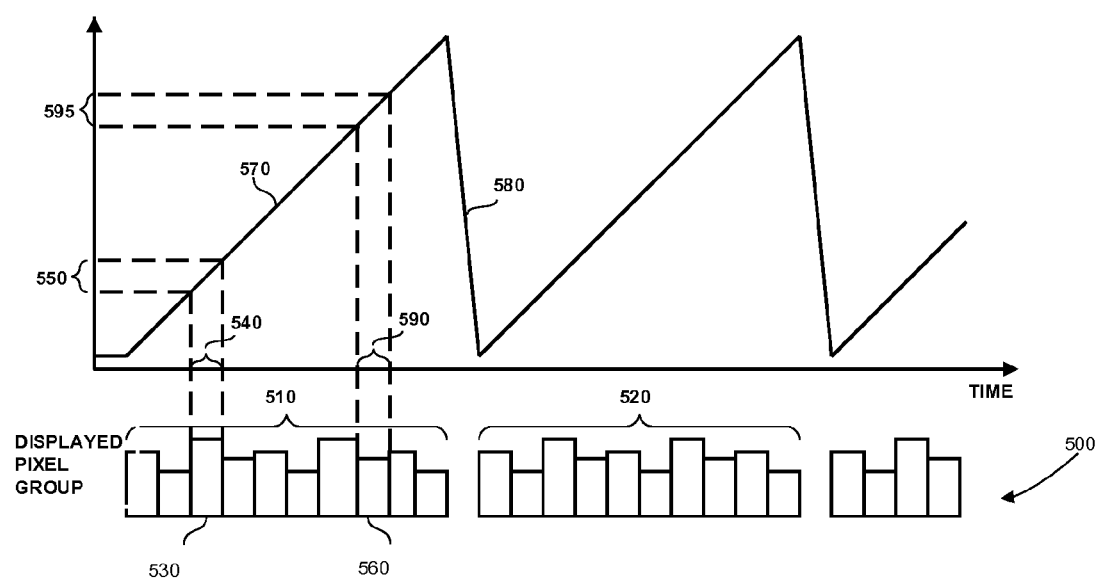
FIG. 5 is a timing diagram illustrating the lens motion and pixel activation for projecting of different groups of pixels at different focal lengths, in accordance with some embodiments of the disclosure.

Referring now to FIG. 5, showing a timing diagram of the lens motion and the corresponding activation of related pixel groups. The horizontal axis represents time, while the vertical axis represents the lens position. The graph shows a linear motion of the lens from the beginning of the range to its end as indicated by line 570, followed by a faster motion back to the starting position as indicated by line 580. It will however be appreciated that any other motion pattern, such as a symmetric motion pattern, where the forward and the backward speed patterns are equal, harmonic sine-like pattern, a piecewise horizontal pattern, where the lens decelerates or stops at predetermined focus positions may be used.

The rectangles generally referenced 500 below the time axis, denote groups of pixels as sequentially activated at the corresponding lens positions. Thus, each of groups 510 and 520 represents all pixels in the image, wherein each separate rectangle such as rectangle 530 or rectangle 560 represent pixels to be projected at a particular focal distance. It will be appreciated that the pixels in each pixel group may or may not be consecutive or neighboring.

When the lens is at a position within a range, for example range 550, which may happen for example at time slot 540, the pixels whose focal distance is within the focus range resulting from lens position within range 550, for example the pixels on group 530, are active, and all other pixels, including group 560 are inactive.

When the lens moves and assumes positions within range 595, for example at time slot 590, pixel group 560 having focal distance within the focus range of positions 595 are active and all other pixels are inactive. The lens movement along the range and back, together with highlighting the relevant pixel group and deactivating other pixel groups at each sub-range, are repeated for each frame. It will be appreciated that unless the displayed image remains the same, the pixel groups change between images, such that different pixels are activated for the same lens position in two different frames.

Figure 6:
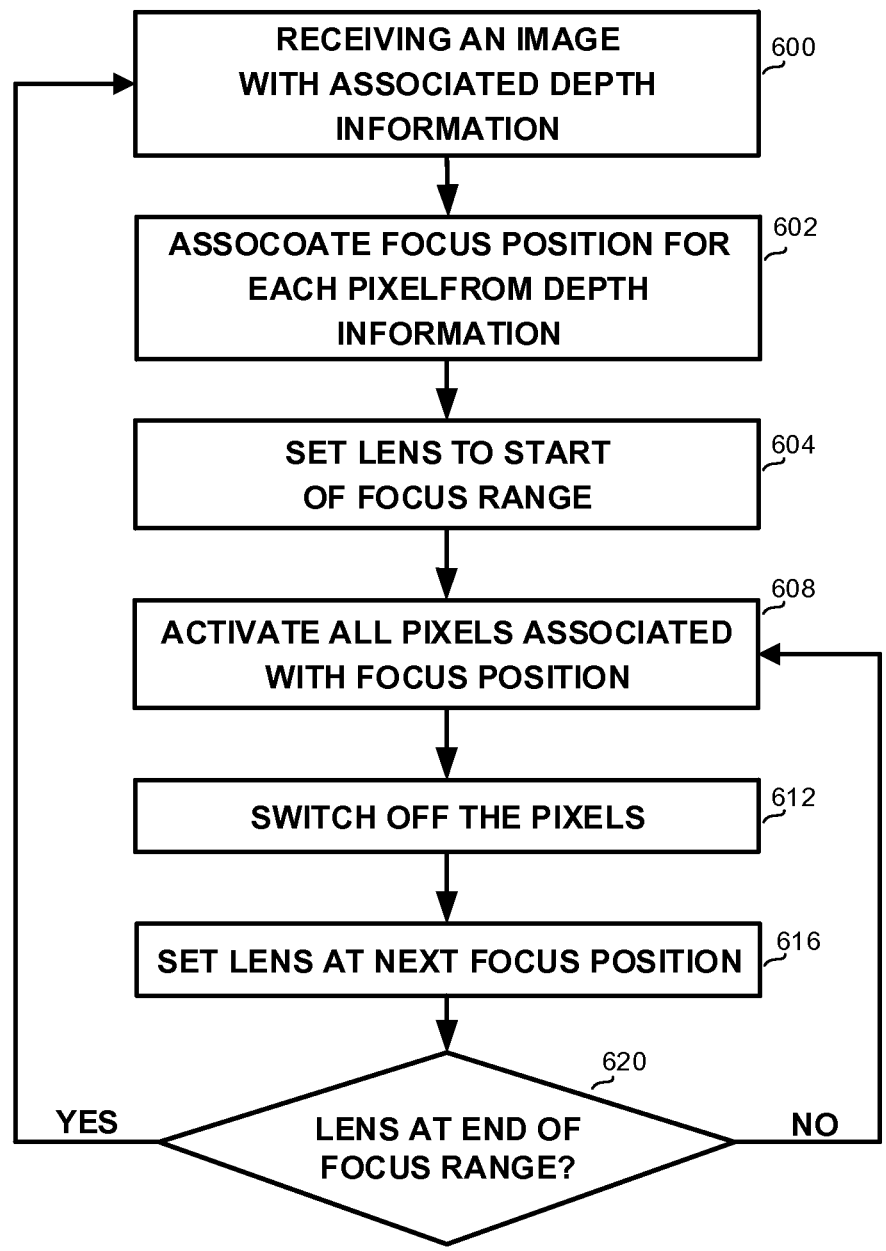
FIG. 6 is a flow chart of a method for displaying different parts of the image at different focal distances in accordance with some embodiments of the disclosure.

Referring now to FIG. 6, showing steps in a flowchart in a method for activating and deactivating pixel groups in accordance with the appropriate focus distance as determined by the lens motion.

On step 600 a frame to be displayed may be received from an external source, via a wired or wireless connection, from the camera or 3D scanner, from a computer game or another video generating software, from memory, or from any other source. The frame may be associated with depth information which may be arranged as a depth map comprising depth information for each pixel in the image. Alternatively, the depth information may be created from data within the image or within a video stream comprising the image such as stereo disparity between the frames of a stereo pair, object size, scene understanding algorithms, focus blur or the like.

On step 602 a depth value associated with each pixel or pixel groups may be translated into a corresponding focal position of the projector.

On step 604, a lens of a projection device may be set at the starting point of its path, at which location it projects images at an initial focus distance. It will be appreciated that if the focal range within an image is smaller than the possible focal range of the projection device, the focal position of the device may be changed only throughout the required range and not its full range.

On step 608 all the pixels attributed to the focus associated with the current position of the lens are projected, e.g. switched on, to a light-emitting state having a nominal brightness level, corresponding to the intended brightness of the pixels in the image.

On step 612, after a predetermined time interval, which may be determined based on the motion speed of the lens, the distribution of focal distance in the image or in the environment or any other parameter, all pixels may be turned off or set to a light-emitting state having a second brightness level lower than the first brightness level.

On step 616 the lens may be set to a next focus position. The lens may be advanced continuously at a uniform or non-uniform speed, at a harmonic modulated speed, stepwise, or in any other manner.

On step 620 it may be determined whether the lens has reached the end of its range. If it has, then all pixel groups have been activated, and execution goes back to step 600 for a new frame to be displayed. Otherwise, execution goes back to step 608 to display the pixel groups relevant for the current lens position. It will be appreciated by a person skilled in the art that as the lens goes back to the initial position, appropriate groups of pixels may also be displayed at appropriate focus positions.

It will be appreciated that it is not necessary to switch off all pixels when the lens is between two positions, furthermore the pixel brightness may vary continuously, for example increase during the lens movement towards the optimal brightness position, and decrease during the movement away from the optimal position, with partially of fully overlapping regions of brightness for different pixels. It will be appreciated that in some embodiments the lens may move harmonically between its extreme focus positions, and each pixel or group of pixels may be displayed at the appropriate focal position or positions during both the forward and the backward course of the lens.

Figure 7:
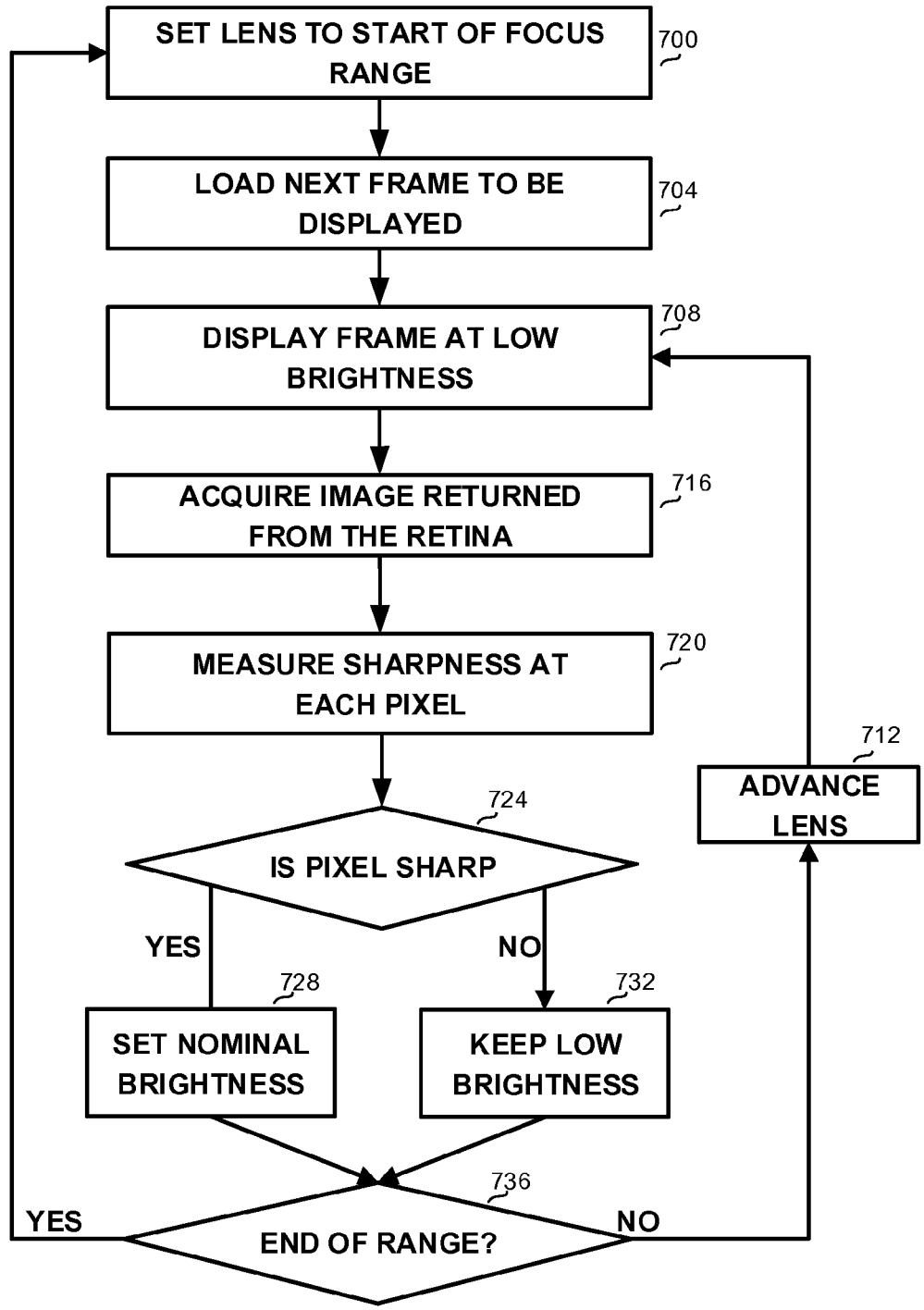
FIG. 7 is a flowchart of steps in a method for projecting images with the use of the feedback camera for adaptive focusing of different parts of the image, in accordance with some embodiments of the disclosure.

Referring now to FIG. 7, showing a flowchart of steps illustrating a method for focusing an image projected onto a user's retina.

On step 700, a lens of a projecting device may be set at the starting point of its path, associated with a starting focus distance of a focus range.

On step 704 the next frame to be displayed may be received or loaded.

On step 708 the frame may be displayed with low brightness value of the pixels. The brightness level of all pixels may be uniform or vary within a range, for example about 0% to about 50% of the maximal brightness.

On step 716 an image reflected back from the user's retina may be acquired by a sensor, for example by using a diagonal semitransparent mirror located between the image projecting component and the retina.

On step 720 the sharpness of each pixel may be determined, and on step 724 it may be determined whether the pixel is sharp, e.g., its sharpness exceeds a threshold.

On step 728, the brightness of pixels that reach the maximal or close to the maximal sharpness at the current lens location is increased, and the pixels may be displayed with brightness that is proportional to the image brightness. Other pixels, which are not in focus, are displayed on step 732 with minimal or low brightness value.

In some embodiments, the lens sweep or motion may be frozen at the position when the image on the retina is sharp. Alternatively, the maximum sharpness position for each pixel is stored in the memory for projection of the next frame during a next focus sweep, or for a later use as an eye and projector calibration data.

On step 736 it may be determined whether the lens is at the end of its range. If not, execution goes to step 712 in which the lens is advanced to a next focus position, and back to step 708 in which the whole frame is displayed with low brightness value.

If the lens is at the end of its range, execution goes back to step 700 and the process restarts for the next frame.

It will be appreciated that the lens may be advanced continuously in a uniform or non-uniform speed, in steps, or in any other manner.

It will be appreciated that the same applications discussed in association with FIG. 3 above may be implemented using the method of FIG. 7.

Figure 8:
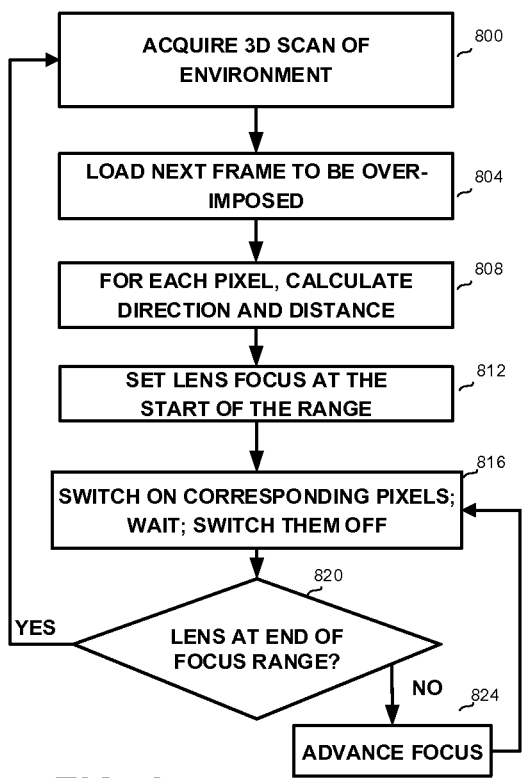
FIG. 8 is a flowchart of steps in a method for presenting augmented reality, in accordance with some embodiments of the disclosure.
Figure 9:
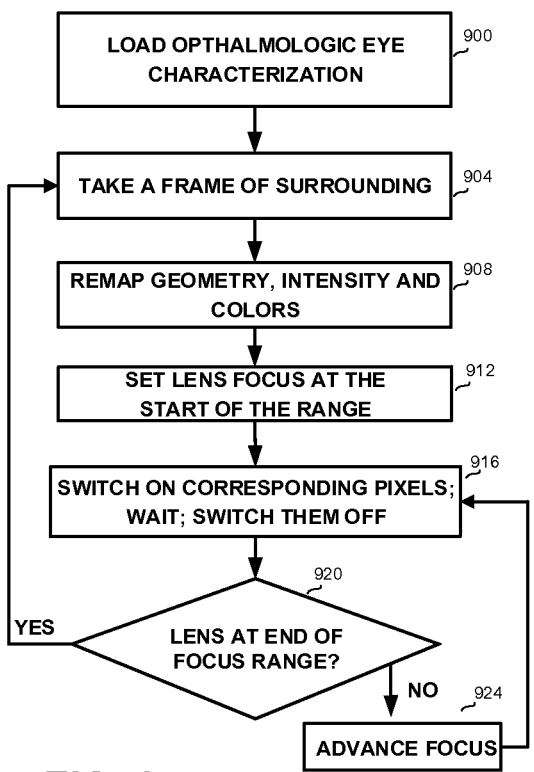
FIG. 9 is a flowchart of steps in a method aiding vision of a user, in accordance with some embodiments of the disclosure.

Referring now to FIG. 8 and FIG. 9 showing flowcharts of steps in applications utilizing pixel activation and deactivation in accordance with the lens position.

Referring now to FIG. 8, showing a flowchart of steps in a method for improving projection of images onto a user's retina, for example during operation of an augmented reality head mounted display overlaying a projected image over the physical environment, in accordance with some embodiments of the disclosure.

On step 800 a 3D scan of the physical environment directly perceived via the HMD may be acquired.

On step 804, a frame to be overlaid onto the environment may be received or loaded.

On step 808, for each pixel of the frame to be overlaid, the distance of the physical object in the environment lying in the same direction in which the pixel should be projected is calculated. For example, if an area of the pixel comprises text to be displayed on a bus, the direction at which the user sees the bus, as well as the distance between the user and the bus may be determined. As detailed in association with step 816 below, the pixel will be activated when the focus distance provided by the lens is equal or close to the required focus length. Thus, a user will see the objects from the environment with overlaid relevant pixels of the image.

On step 812 the lens focus is set to the beginning of its range.

On step 816, the pixels associated with a focus length equal or similar to the focus length of objects within the environment may be switched on, while other pixels may be switched off. After a time interval, for example of about 100 milliseconds or less, or before the lens substantially moves away from appropriate focus position, the pixels may be switched off.

On step 820 it may be determined whether the lens has reached the end of its focus range.

If the lens has reached the end, then execution goes back to step 800 for acquiring a new scan of the environment and loading a next frame to be overlaid.

Otherwise, the lens position is advanced on step 824, and execution goes back to step 816 for switching on the pixels appropriate for the new lens position.

Referring now to FIG. 9, showing a flowchart of steps in a method for using a video projector as a vision aid, in accordance with some embodiments of the disclosure.

On step 900, an ophthalmologic eye characterization may be obtained. The eye characterization may include focal lengths, abnormalities in different parts of the retina, color perception problems, field of view limitations, optical non-uniformities, or the like. Moreover, eye calibration and diagnosis can be performed via software provided with an apparatus in accordance with some embodiments of the disclosure. By displaying specially designed patterns and collecting feedback on the user's perception, feedback given by a user, feedback from image sensors and biosensors or other sensors, an eye characterization can be created, including a map of retina sensitivity, color sensitivity, brightness sensitivity, optical characteristics of the eye and others. An apparatus in accordance with the disclosure may help overcoming some vision impairments and enhance the vision by ways including but not limited to any of the following:

As a result of cerebrovascular accident or other causes, some people may suffer from limited field of view, with some areas of the retina becoming insensitive. Remapping the projected image such that it is projected only onto the light-sensitive parts of the retina will allow vision improvement for people with such vision limitation.

Another common vision limitation is color blindness, when the eye is insensitive to one or more parts of the spectrum. Remapping the colors to fit into the spectrum to which the eye us sensitive will allow vision improvement for the people with such vision limitation. Furthermore, imaging the environment by a cameras and re-projecting the captured video of the environment onto the eye can allow vision enhancement, such as vision in low light conditions, high dynamic range vision, vision with high magnification or extra-wide field of view, including for example simultaneous vision of 360% environment by composing video streams from front- and rear-facing cameras, vision in the infra-red and ultra-violet bands, or the like.

On step 904 a frame of the surrounding of the user may be acquired, for example by an image sensor located close to the user's eye.

On step 908, characteristics of the acquired image may be adjusted in accordance with the ophthalmologic eye characterization received on step 900. Said adjusting may be related to color, geometry, intensity or any other characteristic of the image, according to the ophthalmologic eye characterization. For example, if the person is color-blinded, colors in the image which are problematic for the user may be replaced with other colors.

On step 912, the lens focus of a projector may be set to a starting position, and on step 916 the relevant pixels may be activated. After a time interval, for example of about 100 milliseconds or less, or before the lens substantially moves away from appropriate focus position, the pixels may be switched off.

On step 920 it may be determined whether the lens has reached the end of its focus range.

If it has reached the end, then execution may go back to step 904 for taking another frame of the environment. Otherwise, the focus lens is advanced on step 924, and execution goes back to step 916 for switching on the pixels appropriate for the new lens position.

The method of FIG. 9 demonstrates the operation of a projector as a vision aid device, in which the physical environment is imaged, and images are processed to match the ophthalmologic characteristics of the eye, and projected onto the eyes. This method provides for compensating for arbitrarily complex eye focusing defects, as well as aiding various other vision impairments.

Some vision impairments that can be compensated for, may include optical corrections, including the reproduction or even exceeding of the effect of optical glasses by an optical element as described, for example by using a feedback camera, such as camera 142 of FIG. 3 to control and assure that an image focused on the retina is sharp. The eye optical mapping allows for focusing images, i.e. providing sharp vision even in the cases of severe optical defects of the eye lens, e.g. for cases when different parts of the retina require different focus length.

Another type of correction relates to color correction for people with color blindness, when color distinguishing is enhanced by re-mapping of undistinguished colors into a distinguished color band.

Yet another type of correction may relate to enhancing a limited field of view, by remapping an image captured from the camera onto the active part of the user's retina.

Flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a solid state memory, a hard disk, a random access memory (RAM), a read-only memory (ROM), an erasable programmable read-only memory (EPROM or Flash memory), a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present invention may be written in any combination of one or more programming languages, including an object oriented programming language such as Java, C#, C++ or the like and conventional procedural programming languages, such as the "C", assembly programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), a wired network, a wireless network, a combination thereof, or the like.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for displaying image frames by a projection device, comprising:
   receiving an image frame, with associated depth information;
   determining based on the depth information at least a first group of pixels and a second group of pixels, and for each group of pixels determining a different corresponding focal distance;
   controlling a focusing element, configured to provide a variable focal distance, to sweep periodically, wherein in each time period the focusing element is controlled to sweep throughout a range of provided focal distances; and
   displaying within each time period each of the groups of pixels in different time intervals, each of the groups is displayed at a time interval when the provided focal distance is the corresponding focal distance of that group.

2. The method of claim 1, wherein the projection device is a head mounted display.

3. The method of claim 1, wherein the projection device is an optical head mounted display, allowing to simultaneously perceive the projected video and an environment of the projection device.

4. The method of claim 3, wherein the depth information is computed from the environment underlying the projected image.

5. The method of claim 1, further comprising repeating said receiving, said determining, said controlling and said displaying for a multiplicity of images of a video stream, wherein the video stream is displayed at a frame rate of at about least 10 frames per second.

6. The method of claim 5, wherein
   the video is a stereo video, comprising a left eye channel and a right eye channel, and having stereo disparity between the left eye channel and the right eye channel, wherein
   a first sequence comprising images to be displayed to a left eye of a viewer and a second sequence rising images to be displayed to a right eye of the viewer, are retrieved from the video, wherein
   the depth information is determined from stereo disparity between the images to be displayed to the left eye, and the images to be displayed to the right eye, and wherein
   said displaying comprises projecting the first sequence to the left eye of the viewer, projecting the second sequence is projected to the right eye of the viewer.

7. A projecting system, comprising:
   an active matrix for forming an image to be projected;
   an optical system for projecting the image onto a screen having a focusing element configured to provide a variable focal distance; and
   a hardware processor configured to:
   receive an image frame with associated depth information;
   determine based on the depth information at least a first group of pixels and a second group of pixels, and for each group of pixels determine a different corresponding focal distance;
   control the focusing element to sweep periodically, wherein in each time period the focusing element is controlled to sweep throughout a range of provided focal distances; and
   display within each time period each of the groups of pixels in different time intervals, each of the groups is displayed at a time interval when the provided focal distance is the corresponding focal distance of that group.

8. The projecting system of claim 7, wherein pixels in a first group of pixels in the image are turned on when the optical system assumes a first focus position, and are off at other focus positions, and pixels in a second group of pixels in the image are turned on when the optical system assumes a second focus position and are off at other focus positions.

9. The projecting system of claim 7, wherein a first group of pixels in the image is displayed when the optical system assumes a first focus position and a second group of pixels in the image is displayed when the optical system assumes a second focus position.

\* \* \* \* \*